US010238580B2

(12) United States Patent
Constantine et al.

(10) Patent No.: US 10,238,580 B2
(45) Date of Patent: Mar. 26, 2019

(54) EFFERVESCENT COMPOSITION

(71) Applicant: COSMETIC WARRIORS LIMITED, Poole Dorset (GB)

(72) Inventors: Mark Constantine, Poole (GB); Margaret Joan Constantine, Poole (GB); Helen Elizabeth Ambrosen, Wimborne (GB)

(73) Assignee: COSMETIC WARRIORS LIMITED, Poole, Dorset (GB)

( * ) Notice: Subject to any disclaimer, the term of this patent is extended or adjusted under 35 U.S.C. 154(b) by 0 days.

(21) Appl. No.: 15/116,163

(22) PCT Filed: Mar. 6, 2015

(86) PCT No.: PCT/GB2015/050656
§ 371 (c)(1),
(2) Date: Aug. 2, 2016

(87) PCT Pub. No.: WO2015/136246
PCT Pub. Date: Sep. 17, 2015

(65) Prior Publication Data
US 2017/0172856 A1    Jun. 22, 2017

(30) Foreign Application Priority Data

Mar. 10, 2014 (GB) .................................. 1404178.4
Feb. 4, 2015 (GB) .................................. 1501859.1

(51) Int. Cl.
*A61K 8/02* (2006.01)
*A61K 8/19* (2006.01)
*A61K 8/362* (2006.01)
*A61K 8/60* (2006.01)
*A61K 8/97* (2017.01)
*A61Q 19/10* (2006.01)
*A61K 8/34* (2006.01)
*A61K 8/365* (2006.01)
*A61K 8/20* (2006.01)

(52) U.S. Cl.
CPC ............ *A61K 8/0233* (2013.01); *A61K 8/022* (2013.01); *A61K 8/19* (2013.01); *A61K 8/20* (2013.01); *A61K 8/345* (2013.01); *A61K 8/362* (2013.01); *A61K 8/365* (2013.01); *A61K 8/60* (2013.01); *A61K 8/97* (2013.01); *A61Q 19/10* (2013.01); *A61K 2800/222* (2013.01); *A61K 2800/30* (2013.01); *A61K 2800/33* (2013.01); *A61K 2800/43* (2013.01)

(58) Field of Classification Search
CPC ........ A61K 8/0233; A61K 8/022; A61K 8/19; A61K 8/60; A61K 8/97; A61K 2800/222; A61K 2800/33; A61Q 19/10
See application file for complete search history.

(56) References Cited

U.S. PATENT DOCUMENTS

| 5,602,178 A * | 2/1997 | Caroselli ................. A61K 8/37 514/529 |
| 6,121,215 A * | 9/2000 | Rau ....................... A61K 8/0204 510/130 |
| 6,197,338 B1 * | 3/2001 | Nurnberg ............... A61K 8/375 424/44 |
| 2011/0180445 A1 * | 7/2011 | Hurwitz ............... A61K 8/0216 206/461 |
| 2012/0040919 A1 * | 2/2012 | Constantine ............ A61K 8/19 514/23 |

FOREIGN PATENT DOCUMENTS

| CN | 101467953 A | 7/2009 |
| DE | 19950018 A1 | 4/2001 |
| EP | 0716851 A1 | 6/1996 |
| GB | 2515071 A | 12/2014 |
| WO | 00/47181 A1 | 8/2000 |
| WO | 01/24779 A1 | 4/2001 |
| WO | 2000/28513 A2 | 4/2001 |
| WO | 2008/072104 A2 | 6/2008 |
| WO | 2011/154727 A2 | 12/2011 |

OTHER PUBLICATIONS

Franklin Miller. "Material Bulk Densities." Retrieved Sep. 17, 2017. Retrieved from the internet <URL: https://www.franklinmiller.com/latest-news/material-bulk-densities/>.*
International Search Report and Written Opinion for PCT/GB2015/050656, dated Jun. 2, 2015.
Office Action for Chinese Patent Application No. 2015800130686, dated Jul. 3, 2018.
Examination Report for British Patent Application No. 1501859.1, dated Nov. 16, 2018.

* cited by examiner

*Primary Examiner* — Doan T Phan
(74) *Attorney, Agent, or Firm* — Merchant & Gould P.C.

(57) ABSTRACT

A solid cosmetic product includes an inner non-effervescent material having at least a coloring and a solid carrier material. The solid carrier material is a powder and the non-effervescent material does not effervesce on contact with water. An outer effervescent material is capable of effervescence on contact with water and envelops the inner non-effervescent material.

42 Claims, No Drawings

EFFERVESCENT COMPOSITION

This application is a National Stage of PCT/GB2015/050656, filed 6 Mar. 2015, which claims benefit of 1404178.4, filed 10 Mar. 2014 in Great Britain and 1501859.1, filed 4 Feb. 2015 in Great Britain, which applications are incorporated herein by reference. To the extent appropriate, a claim of priority is made to each of the above disclosed applications.

FIELD OF THE INVENTION

The present invention relates to a cosmetic product, a process for producing said cosmetic product, and a product prepared by the method.

BACKGROUND TO THE INVENTION

The present invention relates to surfactants particularly those for use in contact with the human or animal body.

A bath product which has been increasingly popular is the Bath Bomb® or Ballistic® These products are primarily designed to provide an experience for the user. They contain sodium bicarbonate and citric acid such that on contact with water they effervesce carbon dioxide. This effervescence provides a pleasant sensation for the user. The products also typically contain oils and/or fragrances which are liberated with the effervescence. This liberation adds to the sensory experience of the user.

Surfactant products such as bubble baths, shampoos, shower gels and toothpastes are extremely well known cosmetic products and personal care products. Bubble bath products are typically provided in the form of liquids. They are sold in containers to the end user and may be dispensed by the end user. However, the required use of packaging is a disadvantage. From an environmental perspective, waste packaging is a significant problem, despite the availability of recycling. For this reason at least, solid materials for creating bath foam have become increasingly popular. These solid surfactant materials may be in the form of a Bubble Bar®. For example WO00/47181 discloses a surfactant product bubble bar which is solid and in the form of a tablet or bar. When required for use, a portion of the solid product may be 'broken off' the bar and used. The products of WO00/47181 are formed from a composition containing cream of tartar, sodium bicarbonate and a surfactant. Although these products address environmental concerns they suffer certain disadvantages. For example, in use the user must apply the required amount of product to the bath water, for example by holding the solid product under running water. In this way, the required foam is produced. Furthermore, some users may find that they do not provide the same 'experience' that a bath ballistic may provide.

These problems are addressed in the teaching of WO2011/154727. In this document a two layer bath ballistic type product is disclosed having two effervescent layers. The outer layer is a bath ballistic type material which vigorously effervesces on contact with water and the inner layer is a mixture of bubble bar type material and bath ballistic material. This inner layer contains a surfactant and when contacted with water more gently effervesces than the outer material and thereby gives off bubbles when the water combines with the surfactant.

The present invention seeks to provide products which provide a bath with an enhanced experience by the user.

SUMMARY OF THE INVENTION

In a first aspect, there is provided a solid cosmetic product comprising (i) an inner non-effervescent material comprising at least a colouring and a solid carrier material, wherein the non-effervescent material is a powder, wherein the non-effervescent material does not effervesce on contact with water; (ii) an outer effervescent material, wherein the effervescent material is capable of effervescence on contact with water, wherein the outer effervescent material envelops the inner non-effervescent material.

In a second aspect, there is provided a process for the production of a solid cosmetic product comprising
(i) an inner non-effervescent material comprising at least a colouring and a solid carrier material, wherein the non-effervescent material is a powder, wherein the non-effervescent material does not effervesce on contact with water;
(ii) an outer effervescent material, wherein the effervescent material is capable of effervescence on contact with water, wherein the outer effervescent material envelops the inner non-effervescent material.
the process comprising the steps of:
(a) preparing the inner non-effervescent material comprising at least a colouring and a solid carrier material, wherein the non-effervescent material is a powder, wherein the non-effervescent material does not effervesce on contact with water;
(b) enveloping the inner non-effervescent material with the outer effervescent material, wherein the effervescent material is capable of effervescence on contact with water, wherein the outer effervescent material envelops the inner non-effervescent material.

In a third aspect, there is provided a product obtained or obtainable by a process as described herein.

For ease of reference, these and further aspects of the present invention are now discussed under appropriate section headings. However, the teachings under each section are not necessarily limited to each particular section.

Advantages

We have found that by providing a product containing an inner non-effervescent material which is a powder comprising at least a colouring and a solid carrier material and an outer effervescent material enveloping the inner layer wherein the outer effervescent material envelops the inner non-effervescent material, we are able to provide to the user, for example of bath products, with a product which creates a very pleasant bathing experience may be provided. Typically once a bath has been run the product may be added to the water. This may be before or after the user immersed themselves in the bath. The product is then placed in the water. The sodium bicarbonate and the citric acid in the outer layer of product reacts with water to generate carbon dioxide. This results in an initial effervescence of the product. After a certain period water will penetrate the outer shell of material and enter the core material of the product. The core material is comprised of a solid carrier material which is a coloured powder non-effervescent material. The water mixes with the coloured core and also contacts the inside surface of the shell material. This contact with the effervescent shell material results in generation of carbon dioxide within the inside of the shell. This carbon dioxide expels the mixture of water, colour and carrier from the inside of the product into the bath. The powder nature of the non-effervescent material allows for it to be readily dissolved and/or dispersed by the water. The expelled colour generates patterns within the water (bath) that are pleasant to view and further enhance the experience of the user. Furthermore, by use of a non-effervescing core material, water is readily available to react with the inside surface of the outer shell material. This results in a particularly rapid generation of gas that expels the colouring. This is in contrast with the prior systems where the water reacts with a core material.

DETAILED DESCRIPTION

Composition

As discussed herein, in one aspect of the present invention, there is provided a solid cosmetic product comprising (i) an inner non-effervescent material comprising at least a colouring and a solid carrier material, wherein the non-effervescent material is a powder, wherein the non-effervescent material does not effervesce on contact with water; (ii) an outer effervescent material, wherein the effervescent material is capable of effervescence on contact with water, wherein the outer effervescent material envelops the inner non-effervescent material.

The products of the present invention are compositions which can substantially sustain their physical shape when unsupported by external means, e.g. packaging etc. Thus, they are considered to be solid, solid like, in solid form or in solid-like form at room temperature.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

As mentioned above, due to the solid form of the compositions of the present invention, external packaging is not required to maintain the shape of the composition.

As discussed herein the outer effervescent layer envelops the inner non-effervescent material.

Non-Effervescent Material

The non-effervescent material comprises at least a colouring and a solid carrier material. It will be understood by one skilled in the art that by "non-effervescent material" it is meant a material that does not effervesce on contact with water. As discussed herein, the solid carrier material is a powder and the non-effervescent material is a powder. As will be understood by one skilled in the art a powder is a solid material comprised of particles that are not adhered together. Thus the non-effervescent material does not encompass materials formed from or comprising powders which have been adhered together by compression or other means to form a continuous solid mass.

In one aspect the powder is a free flowing powder. The nature and properties of free flowing powders are known to those skilled in the art. A free flowing powder is one that may flow as a powder under action of gravity.

As discussed herein, to provide the desirable dispersion of the non-effervescent powder material the powder should be able to interact with the water when used. Thus it is desirable that there is little or no adhesion between the powder particles. As adhesion is undesirable in one aspect the non-effervescent material is substantially free of binders. By "substantially free" it is meant in an amount of less than 0.5 wt % based on the non-effervescent material, such as in an amount of less than 0.2 wt % based on the non-effervescent material, such as in an amount of less than 0.1 wt % based on the non-effervescent material, such as in an amount of less than 0.05 wt % based on the non-effervescent material, such as in an amount of less than 0.01 wt % based on the non-effervescent material, such as in an amount of less than 0.005 wt % based on the non-effervescent material, such as in an amount of less than 0.001 wt % based on the non-effervescent material.

Furthermore, to provide the desirable dispersion of the non-effervescent powder material and in particular to reduce or prevent adhesion between the powder particles, the non-effervescent material may further comprise an anti-caking agent. In one aspect the non-effervescent material comprises anti-caking agent in an amount of 0.01 to 10 wt % based on the non-effervescent material, such as in an amount of 0.01 to 8 wt % based on the non-effervescent material, such as in an amount of 0.01 to 6 wt % based on the non-effervescent material, such as in an amount of 0.01 to 4 wt % based on the non-effervescent material, such as in an amount of 0.1 to 4 wt % based on the non-effervescent material, such as in an amount of 1 to 4 wt % based on the non-effervescent material, such as in an amount of 1 to 3 wt % based on the non-effervescent material.

The density of the powder may be selected to provide the required properties of the non-effervescent powder material. It will be understood by one skilled in the art that the density of a powder is measured as bulk density. In one aspect the non-effervescent material has a bulk density of less than 3 g/cm$^3$. In one aspect the non-effervescent material has a bulk density of less than 2.6 g/cm$^3$. In one aspect the non-effervescent material has a bulk density of less than 2.5 g/cm$^3$. In one aspect the non-effervescent material has a bulk density of less than 2 g/cm$^3$. In one aspect the non-effervescent material has a bulk density of less than 1.5 g/cm$^3$. In one aspect the non-effervescent material has a bulk density of less than 1.3 g/cm$^3$. In one aspect the non-effervescent material has a bulk density of less than 0.7 g/cm$^3$. In one aspect the preceding claims wherein the non-effervescent material has a density of less than 0.6 g/cm$^3$.

In one aspect the non-effervescent material has a bulk density of from 3 to 0.4 g/cm$^3$. In one aspect the non-effervescent material has a bulk density of from 2.6 to 0.4 g/cm$^3$. In one aspect the non-effervescent material has a bulk density of from 2.5 to 0.4 g/cm$^3$. In one aspect the non-effervescent material has a bulk density of from 2 to 0.4 g/cm$^3$. In one aspect the non-effervescent material has a bulk density of from 1.5 to 0.4 g/cm$^3$. In one aspect the non-effervescent material has a bulk density of from 1.3 to 0.4 g/cm$^3$. In one aspect the non-effervescent material has a bulk density of from 0.7 to 0.4 g/cm$^3$. In one aspect the preceding claims wherein the non-effervescent material has a density of from 0.6 to 0.4 g/cm$^3$.

The outer effervescent material is typically formed by the adhesion of powders to provide a solid (non-powder) material. For example, the effervescent material may comprise at least sodium bicarbonate and citric acid which are provided in powder form and then compressed together to form a solid. It is therefore desirable for the effervescent material to have density greater than that of the non-effervescent material. In one aspect the non-effervescent material has a density, measured as bulk density, of no greater than 90% of the density of the outer effervescent material. In one aspect the non-effervescent material has a density, measured as bulk density, of no greater than 80% of the density of the outer effervescent material. In one aspect the non-effervescent material has a density, measured as bulk density, of no greater than 70% of the density of the outer effervescent material.

In one aspect the non-effervescent material has a density, measured as bulk density, of from 90% to 60% of the density of the outer effervescent material. In one aspect the non-effervescent material has a density, measured as bulk density, of from 80% to 60% of the density of the outer effervescent material. In one aspect the non-effervescent material has a density, measured as bulk density, of from 70% to 60% of the density of the outer effervescent material.

The solid carrier material may be water soluble or water insoluble. The solid carrier material may be a water soluble powder or water insoluble powder. Preferably the solid carrier material is a water-soluble powder. By water soluble, it is meant a solubility of at least 10 g per 100 g water at 30° C.

Suitable solid carrier materials are powders selected from salt, sugar, sorbitol, cream of tartar, magnesium carbonate, magnesium sulphate, clays and mixtures thereof. Preferred clays are kaolin, Fuller's Earth and bentonite clays. In one aspect the solid carrier material is selected from salt, sugar, sorbitol, cream of tartar and mixtures thereof.

Preferably the salt is sea salt. Preferably the sugar is castor sugar. Indeed these are preferred solid carrier materials. In one aspect the solid carrier material is selected from salt, sugar and mixtures thereof. In one aspect the solid carrier material is selected from sea salt, castor sugar and mixtures thereof. In one aspect the solid carrier material is sea salt. In one aspect the solid carrier material is castor sugar.

Salts are advantageous as they also serve the purpose of providing further functionality to the bathing product. Salts are known to change the osmotic balance of water. This is said to result in less water being absorbed by skin cells, via osmosis. Some bath salts such as phosphates have a detergent action, which softens calloused skin and aids in exfoliation. Some bath salts act as water softeners and change the way soap rinses away. High concentrations of salts increase the density of the water and increase buoyancy. This makes the body feel lighter in the bath. Very high concentrations of salts in water are used in many isolation tank therapies as well as in the treatment of arthritis.

It is preferred that the non-effervescent material is essentially free of surfactant materials. These materials can detract from the display of colour on contact of the product with water.

In one preferred aspect the non-effervescent material contains sodium lauryl sulphate in amount of less than 0.1 wt % based on the non-effervescent material. In one preferred aspect the non-effervescent material contains sodium lauryl sulphate in amount of less than 0.01 wt % based on the non-effervescent material. In one preferred aspect the non-effervescent material contains sodium lauryl sulphate in amount of less than 0.001 wt % based on the non-effervescent material. In one preferred aspect the non-effervescent material is substantially free of sodium lauryl sulphate. In one preferred aspect the non-effervescent material is free of sodium lauryl sulphate.

In one preferred aspect the non-effervescent material contains sodium laureth sulphate in amount of less than 0.1 wt % based on the non-effervescent material. In one preferred aspect the non-effervescent material contains sodium laureth sulphate in amount of less than 0.01 wt % based on the non-effervescent material. In one preferred aspect the non-effervescent material contains sodium laureth sulphate in amount of less than 0.001 wt % based on the non-effervescent material. In one preferred aspect the non-effervescent material is substantially free of sodium laureth sulphate. In one preferred aspect the non-effervescent material is free of sodium laureth sulphate.

In one preferred aspect the non-effervescent material contains sodium lauryl sulphate, sodium laureth sulphate, cocamide diethanolamine and lauryl betaine in a combined amount of less than 0.1 wt % based on the non-effervescent material. In one preferred aspect the non-effervescent material contains sodium lauryl sulphate, sodium laureth sulphate, cocamide diethanolamine and lauryl betaine in a combined amount of less than 0.01 wt % based on the non-effervescent material. In one preferred aspect the non-effervescent material contains sodium lauryl sulphate, sodium laureth sulphate, cocamide diethanolamine and lauryl betaine in a combined amount of less than 0.001 wt % based on the non-effervescent material. In one preferred aspect the non-effervescent material is substantially free of sodium lauryl sulphate, sodium laureth sulphate, cocamide diethanolamine and lauryl betaine. In one preferred aspect the non-effervescent material is free of sodium lauryl sulphate, sodium laureth sulphate, cocamide diethanolamine and lauryl betaine.

In one preferred aspect the non-effervescent material contains surfactant in amount of less than 0.1 wt % based on the non-effervescent material. In one preferred aspect the non-effervescent material contains surfactant in amount of less than 0.01 wt % based on the non-effervescent material. In one preferred aspect the non-effervescent material contains surfactant in amount of less than 0.001 wt % based on the non-effervescent material. In one preferred aspect the non-effervescent material is substantially free of surfactant. In one preferred aspect the non-effervescent material is free of surfactant.

It is preferred that the non-effervescent material further comprises a plant material. For example, the plant material may be selected from herbs, cereals, fruits, flowers and mixtures thereof. In a preferred aspect the non-effervescent material further comprises flowers and in particular petals.

It is preferred that the non-effervescent material further comprises colouring. Preferably the non-effervescent material comprises colouring in an amount of 0.1 to 10 wt % based on the non-effervescent material. Preferably the non-effervescent material comprises colouring in an amount of 0.001 to 3 wt % based on the solid cosmetic product.

The non-effervescent material comprises solid carrier material in amount required to achieve the aims of the invention. Preferably the non-effervescent material comprises solid carrier material in an amount of 50 to 95 wt % based on the non-effervescent material, such as in an amount of 60 to 95 wt % based on the non-effervescent material, such as in an amount of 65 to 95 wt % based on the non-effervescent material, such as in an amount of 70 to 95 wt % based on the non-effervescent material, such as in an amount of 75 to 95 wt % based on the non-effervescent material, such as in an amount of 80 to 95 wt % based on the non-effervescent material, such as in an amount of 85 to 95 wt % based on the non-effervescent material.

In one preferred aspect the non-effervescent material comprises solid carrier material in an amount of 2 to 20 wt % based on the solid cosmetic product. Preferably the non-effervescent material comprises solid carrier material in an amount of 5 to 20 wt % based on the solid cosmetic product, such as in an amount of 10 to 20 wt % based on the solid cosmetic product, such as in an amount of 10 to 15 wt % based on the solid cosmetic product.

In one preferred aspect the non-effervescent material comprises plant material in an amount of 5 to 30 wt % based on the non-effervescent material. Preferably the non-effervescent material comprises plant material in an amount of 10 to 30 wt % based on the non-effervescent material, such as in an amount of 10 to 25 wt % based on the non-effervescent material, such as in an amount of 15 to 25 wt % based on the non-effervescent material, such as in an amount of 15 to 20 wt % based on the non-effervescent material.

In one preferred aspect the non-effervescent material comprises plant material in an amount of 0.01 to 15 wt % based on the solid cosmetic product. Preferably the non-effervescent material comprises plant material in an amount of 0.01 to 10 wt % based on the solid cosmetic product, such as in an amount of 0.01 to 8 wt % based on the solid cosmetic product, such as in an amount of 0.01 to 6 wt % based on the solid cosmetic product, such as in an amount of 0.01 to 4 wt % based on the solid cosmetic product, such as in an amount of 0.1 to 4 wt % based on the solid cosmetic product, such as in an amount of 1 to 4 wt % based on the solid cosmetic product, such as in an amount of 1 to 3 wt % based on the solid cosmetic product.

Effervescent Material

The effervescent material may be selected from appropriate material which effervesce on contact with water. In one aspect the effervescent material comprises at least sodium bicarbonate and citric acid. These materials are present in any suitable amounts to achieve effervescence. One skilled in the art is able to combine these materials to provide the desired rate of effervescence. An alternative to sodium bicarbonate is sodium sesquicarbonate. An alternative to citric acid is tartaric acid.

In a preferred aspect the effervescent material comprises sodium bicarbonate in an amount of 40 to 80 wt % based on the effervescent material. In a preferred aspect the effervescent material comprises sodium bicarbonate in an amount of 40 to 75 wt % based on the effervescent material. In a preferred aspect the effervescent material comprises sodium bicarbonate in an amount of 45 to 70 wt % based on the effervescent material. In a preferred aspect the effervescent material comprises sodium bicarbonate in an amount of 50 to 70 wt % based on the effervescent material. In a preferred aspect the effervescent material comprises sodium bicarbonate in an amount of 55 to 70 wt % based on the effervescent material. In a preferred aspect the effervescent material comprises sodium bicarbonate in an amount of 60 to 70 wt % based on the effervescent material. In a preferred aspect the effervescent material comprises sodium bicarbonate in an amount of approximately 65 wt % based on the effervescent material.

In a preferred aspect the effervescent material comprises sodium bicarbonate in an amount of 35 to 75 wt % based on the solid cosmetic product. In a preferred aspect the effervescent material comprises sodium bicarbonate in an amount of 40 to 75 wt % based on the solid cosmetic product. In a preferred aspect the effervescent material comprises sodium bicarbonate in an amount of 45 to 70 wt % based on the solid cosmetic product. In a preferred aspect the effervescent material comprises sodium bicarbonate in an amount of 50 to 70 wt % based on the solid cosmetic product. In a preferred aspect the effervescent material comprises sodium bicarbonate in an amount of 55 to 70 wt % based on the solid cosmetic product. In a preferred aspect the effervescent material comprises sodium bicarbonate in an amount of 60 to 70 wt % based on the solid cosmetic product. In a preferred aspect the effervescent material comprises sodium bicarbonate in an amount of approximately 65 wt % based on the solid cosmetic product.

In a preferred aspect the effervescent material comprises citric acid in an amount of 20 to 50 wt % based on the effervescent material. In a preferred aspect the effervescent material comprises citric acid in an amount of 25 to 45 wt % based on the effervescent material. In a preferred aspect the effervescent material comprises citric acid in an amount of 25 to 40 wt % based on the effervescent material. In a preferred aspect the effervescent material comprises citric acid in an amount of 25 to 35 wt % based on the effervescent material.

In a preferred aspect the effervescent material comprises citric acid in an amount of 10 to 50 wt % based on the solid cosmetic product. In a preferred aspect the effervescent material comprises citric acid in an amount of 10 to 45 wt % based on the solid cosmetic product. In a preferred aspect the effervescent material comprises citric acid in an amount of 20 to 45 wt % based on the solid cosmetic product. In a preferred aspect the effervescent material comprises citric acid in an amount of 30 to 50 wt % based on the solid cosmetic product. In a preferred aspect the effervescent material comprises citric acid in an amount of 30 to 45 wt % based on the solid cosmetic product. In a preferred aspect the effervescent material comprises citric acid in an amount of 30 to 40 wt % based on the solid cosmetic product.

In a preferred aspect the outer effervescent material further comprises a colouring. For example the outer effervescent material may comprise colouring in an amount of 0.001 to 3 wt % based on the solid cosmetic product.

In one aspect the outer effervescent material further comprises a surfactant. The surfactant may be any suitable surfactant. For example, the surfactant may be selected from sodium lauryl sulphate, sodium laureth sulphate, cocamide diethanolamine, lauryl betaine and mixtures thereof. The surfactant, if present, may be present in any suitable amount. In one aspect the outer effervescent material contains surfactant in amount of from 0.2 to 10% based on the based on the solid cosmetic product.

In one aspect the outer effervescent material is essentially free of surfactant materials.

In one aspect the outer effervescent material contains sodium lauryl sulphate in amount of less than 0.1 wt % based on the outer effervescent material. In one aspect the outer effervescent material contains sodium lauryl sulphate in amount of less than 0.01 wt % based on the outer effervescent material. In one aspect the outer effervescent material contains sodium lauryl sulphate in amount of less than 0.001 wt % based on the outer effervescent material. In one aspect the outer effervescent material is substantially free of sodium lauryl sulphate. In one aspect the outer effervescent material is free of sodium lauryl sulphate.

In one aspect the outer effervescent material contains sodium laureth sulphate in amount of less than 0.1 wt % based on the outer effervescent material. In one aspect the outer effervescent material contains sodium laureth sulphate in amount of less than 0.01 wt % based on the outer effervescent material. In one aspect the outer effervescent material contains sodium laureth sulphate in amount of less than 0.001 wt % based on the outer effervescent material. In one aspect the outer effervescent material is substantially free of sodium laureth sulphate. In one aspect the outer effervescent material is free of sodium laureth sulphate.

In one aspect the outer effervescent material contains sodium lauryl sulphate, sodium laureth sulphate, cocamide diethanolamine and lauryl betaine in a combined amount of less than 0.1 wt % based on the outer effervescent material. In one aspect the outer effervescent material contains sodium lauryl sulphate, sodium laureth sulphate, cocamide diethanolamine and lauryl betaine in a combined amount of less than 0.01 wt % based on the outer effervescent material. In one aspect the outer effervescent material contains sodium lauryl sulphate, sodium laureth sulphate, cocamide diethanolamine and lauryl betaine in a combined amount of less than 0.001 wt % based on the outer effervescent material. In one aspect the outer effervescent material is substantially free of sodium lauryl sulphate, sodium laureth sulphate, cocamide diethanolamine and lauryl betaine. In one aspect the outer effervescent material is free of sodium lauryl sulphate, sodium laureth sulphate, cocamide diethanolamine and lauryl betaine.

In one aspect the outer effervescent material contains surfactant in amount of less than 0.1 wt % based on the outer effervescent material. In one aspect the outer effervescent material contains surfactant in amount of less than 0.01 wt % based on the outer effervescent material. In one aspect the outer effervescent material contains surfactant in amount of less than 0.001 wt % based on the outer effervescent material. In one aspect the outer effervescent material is substantially free of surfactant. In one aspect the outer effervescent material is free of surfactant.

In a preferred aspect the effervescent material further comprises a fragrance. Preferably the fragrance is present in an amount of 0.5 to 4 wt % based on the effervescent material. In a preferred aspect the effervescent material comprises fragrance in an amount of 1 to 4 wt % based on the effervescent material. In a preferred aspect the effervescent material comprises fragrance in an amount of 2 to 4 wt % based on the effervescent material. In a preferred aspect the effervescent material comprises fragrance in an amount of 2.5 to 3.5 wt % based on the effervescent material. In a preferred aspect the effervescent material comprises fragrance in an amount of approximately 3 wt % based on the effervescent material.

The density of the effervescent material components and the combination of the same may be selected to provide the required properties of the effervescent material. In one aspect the effervescent material has a density of less than 3 g/cm$^3$. In one aspect the effervescent material has a density of less than 2.6 g/cm$^3$. In one aspect the effervescent material has a density of less than 2.5 g/cm$^3$. In one aspect the effervescent material has a density of less than 2 g/cm$^3$. In one aspect the effervescent material has a density of from 3 to 1.5 g/cm$^3$. In one aspect the effervescent material has a density of from 2.6 to 1.5 g/cm$^3$. In one aspect the effervescent material has a density of from 2.5 to 1.5 g/cm$^3$. In one aspect the effervescent material has a density of from 2 to 1.5 g/cm$^3$.

Product

The effervescent material and the non-effervescent material are combined to prepare a product in accordance with the present invention. The product may of course contain components in addition to the effervescent material and the non-effervescent material. However, in one aspect the product consists of the effervescent material and the non-effervescent material.

The effervescent material and the non-effervescent material may be combined in any suitable ratio to provide the desired product. Preferred ratios (based on weight) of effervescent material to non-effervescent material are 9:1 to 1:9, 9:1 to 1:4, 9:1 to 1:2, 9:1 to 1:1, 9:1 to 2:1, 9:1 to 4:1, 9:1 to 6:1, and 9:1 to 6:1, One skilled in the art can readily prepare a product based on these ratios and the amounts of materials based on the effervescent and non-effervescent materials.

The components of the product may be selected such that the final product has a density of less than 3 g/cm$^3$, such as less than 2.5 g/cm$^3$, less than 2 g/cm$^3$.

Each of the effervescent material and the non-effervescent material may optionally contain colouring independently of each other. When both materials contain colouring the colours may be selected such that a colour in the outer material is dispersed in the water in use. When the water penetrates to the inner material a non-colour may be dispersed. If this non-effervescent colour is different to the effervescent colour it will combine with the effervescent colour to provide a change of colour to the water.

Process

As discussed herein, the invention provides a process for the production of a product described herein comprising the steps of:

(i) preparing the inner non-effervescent material comprising at least a colouring and a solid carrier material, wherein the non-effervescent material is a powder, wherein the non-effervescent material does not effervesce on contact with water;

(ii) enveloping the inner non-effervescent material with the outer effervescent material, wherein the effervescent material is capable of effervescence on contact with water, wherein the outer effervescent material envelops the inner non-effervescent material.

In one aspect of the present process the process comprises the steps of:

i) preparing the non-effervescent material;
ii) enveloping the non-effervescent material with the effervescent material.

As discussed below in further detail, a preferred method of preparing a product in accordance with the present invention is to provide more than one section of outer effervescent material. For example, two hemi spherical sections may be provided. Within one or more of these sections a recess or indentation may be provide to receive non-effervescent material. For example, into one or both hemi spherical sections an indentation may be provided in the centre of the circular face of the hemisphere. Non-effervescent powder material is then placed into the recess or indentation. The sections are then brought together. For example, the two hemi spherical sections may be adhered together to form a sphere. Thus in one preferred aspect the process of the invention comprises the steps of (i) forming a plurality of sections of outer effervescent material;

(ii) providing in one or more of the sections of outer effervescent material a recess for non-effervescent material;

(iii) inserting non-effervescent material in the recess in the outer effervescent material; and (iv) combining the plurality of sections of outer effervescent material to envelope the inner non-effervescent material with the outer effervescent material.

Preferably the non-effervescent material of step i) is caused to solidify in a predetermined shape. After the solidification the non-effervescent material of step i) the effervescent material, is placed around the solid so as to envelop it. The effervescent material of step ii) is also typically caused to solidify in a predetermined shape. Possible shapes include spheres, cube, cuboids and cones.

The shape of the products of the present invention is not limited. It may be that the products are provided with a shape which would be aesthetically pleasing and/or which aids in the use of the product. For example, it may be that the product is produced in such a manner so that it solidifies in a shape which is ergonomically acceptable to the user. Therefore, in one embodiment of the process of the present invention, the mixture of step i) and/or step ii) is pressed into a mould, allowed to solidify, and then turned out to produce the product.

As described herein, the product may further comprise one or more cosmetically acceptable additives. In one embodiment, the process further comprises the step of combining with the mixture of step i) and/or step ii) one or more cosmetically acceptable additives as defined above.

In the general method of the invention the following composition is prepared

| Formula wt % | Raw Material Type |
|---|---|
| | Shell: |
| 45.0-80.0 | Sodium Bicarbonate |
| 0.001-3.0 | Colour |
| 0.1-5.0 | Fragrance |
| 10.0-45.0 | Citric Acid |
| | Core Contents: |
| 2.0-20.0 | Sea Salt/Castor Sugar/Sorbitol |
| 0.001-3.0 | Colour |
| 0.01-15.0 | Herbs/Cereals/Fruits/Flowers |

Method
1. Mix the Bicarbonate Phase with the colour and fragrance to ensure even distribution
2. Sieve the Acid phase into the bicarbonate phase and mix thoroughly.
3. Fill the moulds with the bicarbonate: acid mix and hollow the centre of the moulds.
4. Fill the hollow centres with the core mix and press together.

Preferred Compositions & Additional Components

The product of the present invention may also comprise one or more cosmetically acceptable additives. The person skilled in the art is aware of a range of cosmetically acceptable additives which are suitable for incorporation into such compositions. Fruit and herb extracts and juices, vegetable oils and essential oils are all compatible with the composition. Colours, both naturally derived and synthetic can be used to colour the product. Sodium carbonate may also incorporated into the composition.

In one embodiment, the cosmetically acceptable additives are selected from the group consisting of essential oils, vitamins, fragrances, colourings, clays, vegetable butters, decorative articles and mixtures thereof.

In one embodiment, the cosmetically acceptable additives are present in amount of from about 0.2% to about 3% by weight of the total composition.

The essential oils will be selected based on the fragrance desired, skin type to be treated and other effects desired based on the well-known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the product are selected from Tarragon, Lemon myrtle, Jasmin, Ylang ylang, Labdunum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, *Litsea Cubeba*, Cardamon, Tonka, and Chamomile blue. In one embodiment, the one or more essential oils present in the product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the product of a material, such as a natural material, that has a high vitamin content.

The ingredients in the present invention do not require cosmetic preservatives. The use of cosmetic preservatives can increase the potential to irritate the skin.

The decorative items which may be present in the product include items such as glitter, paper such as rice paper, sequins, dried or fresh flowers, herbs, vegetables, parts thereof or mixtures thereof. Other enhancing materials such as popping candy may also be incorporated The above ranges provide preferred amounts of each of the components. Each of these ranges may be taken alone or combined with one or more other component ranges to provide a preferred aspect of the invention.

Method

In one aspect of the present invention, there is provided a method comprising contacting the skin of a user with water in which the product as defined herein has dissolved or in which the product as defined herein is dissolving. In a typical method water in run in to the bath at acceptable temperature. The user immerses their body in the water and the product is dropped in to the water. The user then watches the effect of the product on the surface of the water or as it effervesces beneath the surface. The user then bathes in the water.

Further Broad Aspects

In a first broad aspect, there is provided a solid cosmetic product comprising (i) an inner non-effervescent material comprising at least a colouring and a solid carrier material, wherein the non-effervescent material does not effervesce on contact with water; (ii) an outer effervescent material, wherein the effervescent material is capable of effervescence on contact with water, wherein the outer effervescent material envelops the inner non-effervescent material.

In a second broad aspect, there is provided a process for the production of a solid cosmetic product comprising
  (i) an inner non-effervescent material comprising at least a colouring and a solid carrier material, wherein the non-effervescent material does not effervesce on contact with water;
  (ii) an outer effervescent material, wherein the effervescent material is capable of effervescence on contact with water, wherein the outer effervescent material envelops the inner non-effervescent material.
the process comprising the steps of:
(a) preparing the inner non-effervescent material comprising at least a colouring and a solid carrier material, wherein the non-effervescent material does not effervesce on contact with water;
(b) enveloping the inner non-effervescent material with the outer effervescent material, wherein the effervescent material is capable of effervescence on contact with water, wherein the outer effervescent material envelops the inner non-effervescent material.

In a third broad aspect, there is provided a product obtained or obtainable by a process as described herein.

Examples

The invention will now be described with reference to the following non-limiting example.

A product having the following composition was prepared.

The formula is as follows:

| Formula % | Raw Material Type | Mass (g) |
|---|---|---|
| | Shell: | |
| 56.80 | Sodium Bicarbonate-Technical | 56.800 |
| 0.10 | Colour | 0.100 |
| 1.00 | Fragrance | 1.000 |
| 30.00 | Citric Acid | 30.000 |
| | Core Contents: | |
| 10.00 | Sea Salt | 10.000 |
| 0.10 | Colour | 0.100 |
| 2.00 | Dried Flowers | 2.000 |
| 100.00 | | 100.000 |

Method
Bicarbonate Mix:
1. Weigh the Sodium Bicarbonate into the mixer
2. Add Fragrance and Colour and mix thoroughly Salt Mix:
3. Weigh the Salt into the mixer
4. Add the Colour gradually and mix to disperse until evenly coated
5. Sieve the Citric Acid, add to the Bicarb mix and mix thoroughly
6. Fill each half mould with mix and hollow out the centre to create a shell.
7. Fill the cavity in each half mould with the Dried Flowers and coloured Salt then press together
8. Leave to set then turn out of moulds After production the product was used in a bath. The product was immersed in water and the outer shell effervesced. After a short time, water penetrated the outer shell—this was apparent from the rapid jet of coloured water and flowers that were propelled from the core of the product. The user rated highly the visual effect of the product.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid cosmetic product comprising:
(i) an inner non-effervescent material comprising at least a colouring and a solid carrier material, wherein the non-effervescent material is a free-flowing powder, wherein the non-effervescent material does not effervesce on contact with water;
wherein the non-effervescent material has a bulk density of less than 3 g/cm$^3$;
wherein the non-effervescent material comprises solid carrier material in an amount of at least 50 wt % based on the non-effervescent material; and
wherein the non-effervescent material comprises solid carrier material in an amount of 2 to 20 wt % based on the solid cosmetic product; and
(ii) an outer effervescent material, wherein the effervescent material is capable of effervescence on contact with water,
wherein the outer effervescent material envelops the inner non-effervescent material; and
wherein the ratio based on weight of effervescent material to non-effervescent material is from 9:1 to 1:1.

2. The solid cosmetic product according to claim 1, wherein the outer effervescent material entirely envelops the inner non-effervescent material.

3. The solid cosmetic product according to claim 1, wherein the solid carrier material is selected from the group consisting of salt, sugar, sorbitol, cream of tartar, magnesium carbonate, magnesium sulphate, clays, and mixtures thereof.

4. The solid cosmetic product according to claim 3, wherein the salt is sea salt.

5. The solid cosmetic product according to claim 3, wherein the sugar is castor sugar.

6. The solid cosmetic product according to claim 1, wherein the solid carrier material is a water-soluble powder.

7. The solid cosmetic product according to claim 1, wherein the non-effervescent material further comprises a plant material.

8. The solid cosmetic product according to claim 7, wherein the plant material is selected from the group consisting of herbs, cereals, fruits, flowers and mixtures thereof.

9. The solid cosmetic product according to claim 1, wherein the non-effervescent material is substantially free of surfactant.

10. The solid cosmetic product according to claim 1, wherein the non-effervescent material is substantially free of binders.

11. The solid cosmetic product according to claim 1, wherein the non-effervescent material further comprises an anti-caking agent.

12. The solid cosmetic product according to claim 1, wherein the non-effervescent material has a density of less than 1.3 g/cm$^3$.

13. The solid cosmetic product according to claim 1, wherein the non-effervescent material has a density of less than 0.7 g/cm$^3$.

14. The solid cosmetic product according to claim 1, wherein the non-effervescent material has a density of less than 0.6 g/cm$^3$.

15. The solid cosmetic product according to claim 1, wherein the non-effervescent material has a density of no greater than 90% of the density of the outer effervescent material.

16. The solid cosmetic product according to claim 1, wherein the non-effervescent material has a density of no greater than 80% of the density of the outer effervescent material.

17. The solid cosmetic product according to claim 1, wherein the powder is selected from the group consisting of salt, sugar, sorbitol, cream of tartar and mixtures thereof.

18. The solid cosmetic product according to claim 1, wherein the non-effervescent material comprises colouring in an amount of 0.1 to 10 wt % based on the non-effervescent material.

19. The solid cosmetic product according to claim 1, wherein the non-effervescent material comprises colouring in an amount of 0.001 to 3 wt % based on the solid cosmetic product.

20. The solid cosmetic product according to claim 1, wherein the non-effervescent material comprises solid carrier material in an amount of 50 to 95 wt % based on the non-effervescent material.

21. The solid cosmetic product according to claim 1, wherein the non-effervescent material comprises solid carrier material in an amount of 2 to 20 wt % based on the solid cosmetic product.

22. The solid cosmetic product according to claim 7, wherein the non-effervescent material comprises plant material in an amount of 5 to 30 wt % based on the non-effervescent material.

23. The solid cosmetic product according to claim 7, wherein the non-effervescent material comprises plant material in an amount of 0.01 to 15 wt % based on the solid cosmetic product.

24. The solid cosmetic product according to claim 1, wherein the outer effervescent material comprises at least sodium bicarbonate and citric acid.

25. The solid cosmetic product according to claim 1, wherein the outer effervescent material comprises sodium bicarbonate in an amount of 45 to 80 wt % based on the outer effervescent material.

26. The solid cosmetic product according to claim 1, wherein the outer effervescent material comprises sodium bicarbonate in an amount of 35 to 75 wt % based on the solid cosmetic product.

27. The solid cosmetic product according to claim 1, wherein the outer effervescent material comprises citric acid in an amount of 20 to 50 wt % based on the outer effervescent material.

28. The solid cosmetic product according to claim 1, wherein the outer effervescent material comprises citric acid in an amount of 10 to 45 wt % based on the solid cosmetic product.

29. The solid cosmetic product according to claim 1, wherein the outer effervescent material further comprises colouring.

30. The solid cosmetic product according to claim 29 wherein the outer effervescent material comprises colouring in an amount of 0.001 to 3 wt % based on the solid cosmetic product.

31. The solid cosmetic product according to claim 1, wherein the solid cosmetic product has a density of less than 1 g/cm$^3$.

32. The solid cosmetic product according to claim 1, wherein the inner non-effervescent material is present in an amount of 2 to 40 wt % based on the solid cosmetic product.

33. The solid cosmetic product according to claim 1, wherein the outer effervescent material is present in an amount of 60 to 98 wt % based on the solid cosmetic product.

34. A process for producing the solid cosmetic product according to claim 1, comprising the steps of:
   (i) preparing the inner non-effervescent material comprising at least a colouring and a solid carrier material; and
   (ii) enveloping the inner non-effervescent material with the outer effervescent material.

35. The process according to claim 34, wherein the effervescent material of step (ii) is caused to solidify in a predetermined shape.

36. A process for producing the solid cosmetic product according to claim 1, comprising the steps of:
   (i) forming a plurality of sections of outer effervescent material;
   (ii) providing in one or more of the sections of outer effervescent material a recess for non-effervescent material;
   (iii) inserting non-effervescent material in the recess in the outer effervescent material; and
   (iv) combining the plurality of sections of outer effervescent material to envelope the inner non-effervescent material with the outer effervescent material.

37. The solid cosmetic product according to claim 1, wherein the ratio based on weight of effervescent material to non-effervescent material is from 9:1 to 2:1.

38. The solid cosmetic product according to claim 1, wherein the ratio based on weight of effervescent material to non-effervescent material is from 9:1 to 4:1.

39. The solid cosmetic product according to claim 1, wherein the ratio based on weight of effervescent material to non-effervescent material is from 9:1 to 6:1.

40. The solid cosmetic product according to claim 1, wherein the solid cosmetic product is a bathing product.

41. The solid cosmetic product according to claim 1, wherein the non-effervescent material contains binders in an amount of less than 0.5 wt % based on the non-effervescent material.

42. The solid cosmetic product according to claim 1, wherein the non-effervescent material consists of (a) a colouring, (b) a solid carrier material and (c) cosmetically acceptable additives selected from the group consisting of essential oils, vitamins, fragrances, colourings, clays, vegetable butters, decorative articles and mixtures thereof.

* * * * *